United States Patent [19]

Sato et al.

[11] 4,416,772

[45] Nov. 22, 1983

[54] APPARATUS FOR CONCENTRATING AND FILTERING BODY CAVITY FLUIDS

[75] Inventors: Takashi Sato, Kanazawa; Makoto Mukai, Fukui; Shiro Nagata, Kurashiki; Yoshimichi Harada, Okayama; Yasuzo Kirita, Toyonaka, all of Japan

[73] Assignee: Kuraray Co., Ltd., Kurashiki, Japan

[21] Appl. No.: 286,625

[22] Filed: Jul. 24, 1981

[30] Foreign Application Priority Data

Aug. 4, 1980 [JP] Japan .............................. 55-107331

[51] Int. Cl.³ ............................................. B01D 31/00
[52] U.S. Cl. ............................. 210/137; 128/DIG. 3; 210/195.2; 210/257.2; 210/266; 604/27
[58] Field of Search ............... 128/213 A, 213 R, 227, 128/DIG. 3; 210/137, 195.2, 257.2, 321.3, 340, 645, 646, 647, 648; 604/317–322, 403, 406, 27

[56] References Cited

U.S. PATENT DOCUMENTS

| 3,648,698 | 3/1972 | Doherty | 604/319 |
| 3,799,873 | 3/1974 | Brown | 210/648 |
| 4,190,047 | 2/1980 | Jacobsen et al. | 210/646 |
| 4,240,408 | 12/1980 | Schael | 128/213 A |
| 4,269,708 | 5/1981 | Bonomini et al. | 210/257.2 |
| 4,311,587 | 1/1982 | Nose et al. | 128/213 A |

Primary Examiner—William E. Kamm
Assistant Examiner—George Yanulis
Attorney, Agent, or Firm—Barry Kramer

[57] ABSTRACT

Body cavity fluids, such as ascitic fluid and pleural fluid, are concentrated and filtered to remove bacteria and cancer cells, and the filtered concentrate is returned to the patient intravenously. The concentration and filtration are performed batch-wise, with the concentration being done before the filtration. The apparatus for concentrating and filtering includes a first container for holding the body fluid, a second container for holding the final filtered concentrate, a filter, a concentrator, a pump and two branched tubes connected to the filter and the concentrator which tubes can be selectively closed for concentrating and filtering the body fluid. The fluid outlet of the first container is designed to help prevent precipitated fibrin from passing out of the container and blocking the concentrator or filter membranes.

4 Claims, 6 Drawing Figures

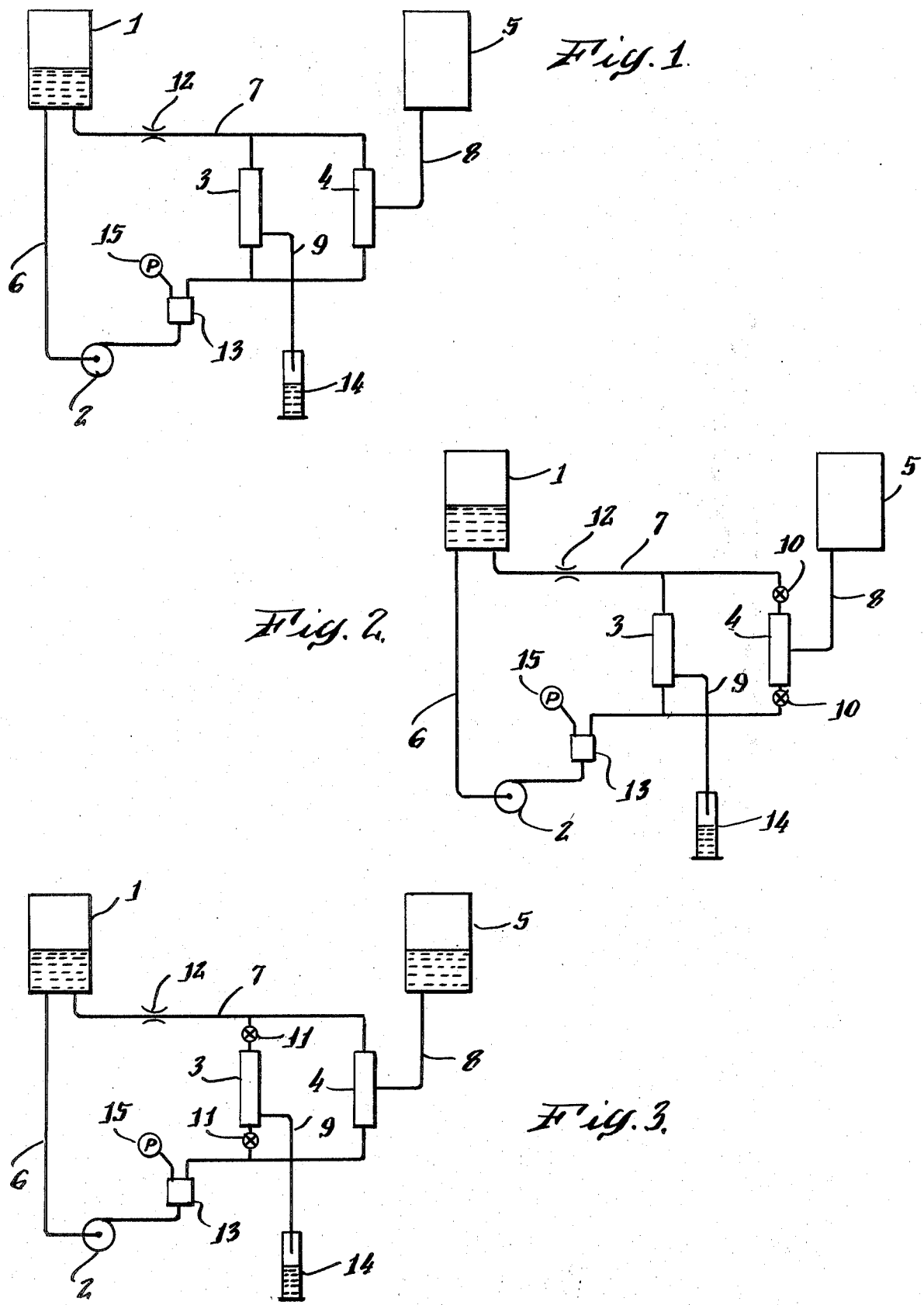

APPARATUS FOR CONCENTRATING AND FILTERING BODY CAVITY FLUIDS

BACKGROUND OF THE INVENTION

1. Field of the Invention

This invention relates to a novel apparatus which is capable of treating body cavity fluids very efficiently and safely by the batch-wise concentration of body cavity fluids followed by filtration. The term "body cavity fluids" as used herein includes protein-containing fluids accumulated and retained in body cavities, such as ascitic fluid and pleural fluid.

2. Description of the Prior Art

There are a considerable number of patients who are suffering from hydrops of body cavities, such as ascites and hydrothorax, resulting from cirrhosis, renal failure or cancer of the viscera, among others. Recently, an apparatus for filtering and concentrating ascitic fluid for returning the concentrate intravenously to the patient has been proposed (see, for example, Japanese Patent Publication No. 80-15221). In such apparatus, ascitic fluid withdrawn from the abdominal cavity of an ascitic patient is filtered through a hollow fiber filter whereby cancer cells or bacteria are removed. The filtrate ascitic fluid is then concentrated by means of a hollow fiber concentrator to increase the concentration of useful proteins, and the resulting concentrated ascitic fluid is returned intravenously to the patient. This type of apparatus was developed to provide a safer system capable of overcoming the deficiencies of the prior art ascitic fluid-concentrating apparatus wherein, when unnecessary material such as bacteria and giant cells were present in the ascitic fluid, these too were also concentrated and returned to the patient.

However, there are further disadvantages associated with the above-mentioned ascitic fluid filtering and concentrating apparatus in that complicated control mechanisms are required for associated control of filtration and concentration and for control of the rate of concentration; and still further, two or more pumps are required so that the apparatus is complicated, troublesome to operate, large-sized and expensive.

SUMMARY OF THE INVENTION

It is an object of the invention to overcome the disadvantages of the above-mentioned apparatus and provide a body cavity fluid treating apparatus which can be handled and operated in a simple and easy manner. Another object is to provide a small-sized and inexpensive body cavity fluid treating apparatus.

BRIEF DESCRIPTION OF THE DRAWINGS

In the accompanying drawings,

FIG. 1 is a schematic illustration of an embodiment of the body cavity fluid treating apparatus of the present invention;

FIG. 2 is a schematic illustration of one mode of operation of the apparatus wherein a body cavity fluid is being concentrated in said body cavity fluid treating apparatus;

FIG. 3 is a schematic illustration of another mode of operation wherein a body cavity fluid is being filtered through a filter;

DETAILED DESCRIPTION OF THE INVENTION

Figure 4:
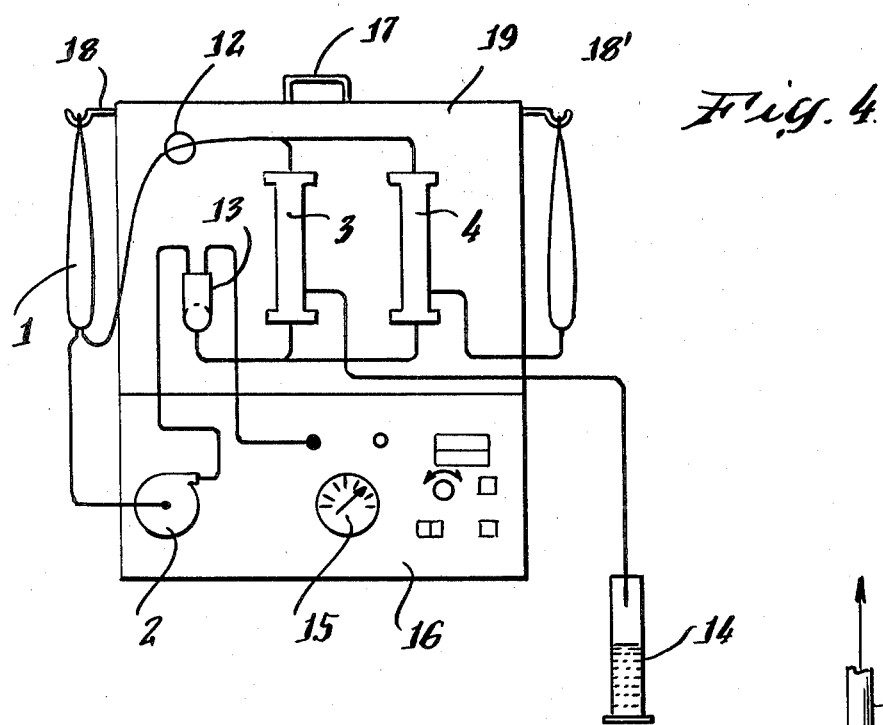
FIG. 4 is a front elevation of one embodiment of the body cavity fluid treating apparatus of the present invention.

The present invention provides a body cavity fluid treating apparatus which comprises a first container for holding a body cavity fluid, a second container for holding a concentrated body cavity fluid freed from bacteria, a pump for drawing out the body cavity fluid from the first container, a concentrator for concentrating the body cavity fluid, a filter for filtering the body cavity fluid which has been concentrated in said concentrator, a first flow path connecting the first container with the body cavity fluid inlet of the concentrator and with the body cavity fluid inlet of the filter by means of a branched tube, a second flow path connecting the body cavity fluid outlet of the concentrator and the body cavity fluid outlet of the filter respectively with the first container by means of a branched tube, a third flow path connecting the filtrate outlet of the filter with the second container, a fourth flow path connected to the filtrate outlet of the concentrator, means for closing, during the period of body cavity fluid concentration, those branches of the branched tubes in the first and second flow paths which are connected to the inlet and outlet of the filter, respectively, and closing, during the period of body cavity fluid filtration, those branches of the branched tubes in said same flow paths which are connected to the inlet and outlet of the concentrator, respectively, and a pressure regulating means provided in said second flow path.

A novel feature of the present invention consists in batch-wise body cavity fluid concentration and filtration. Employment of such batch-wise treatment has made it possible to provide an apparatus which is easy to use, simple to operate and free from errors.

Another novel feature of the invention lies in that concentration is performed prior to filtration; whereas, in the prior art, filtration procedes concentration. Thus, the invention has made it possible to utilize common flow paths for concentration and filtration which is impossible in the prior art apparatus. In accordance with the present invention, only one pump is required, consequently the apparatus is small-sized and inexpensive, and troublesome operation, one of the great drawbacks heretofore associated with this kind of apparatus, is greatly reduced.

Referring to the drawings, FIG. 1 illustrates a schematic flow diagram of the apparatus of the invention. A container 1 for holding a body cavity fluid removed from a living body, a pump 2 for transporting the body cavity fluid, a concentrator 3, a filter 4, and a container 5 for holding the concentrated and filtered body cavity fluid are essential elements of the apparatus of the invention and are interconnected by common flow paths.

Figure 5:
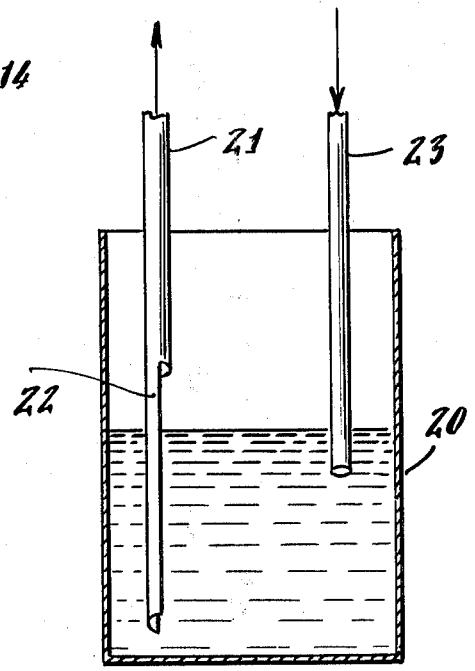
FIG. 5 is a schematic illustration of a preferred example of the body cavity fluid holding container to be used in the body cavity fluid treating apparatus of the present invention.
Figure 6:
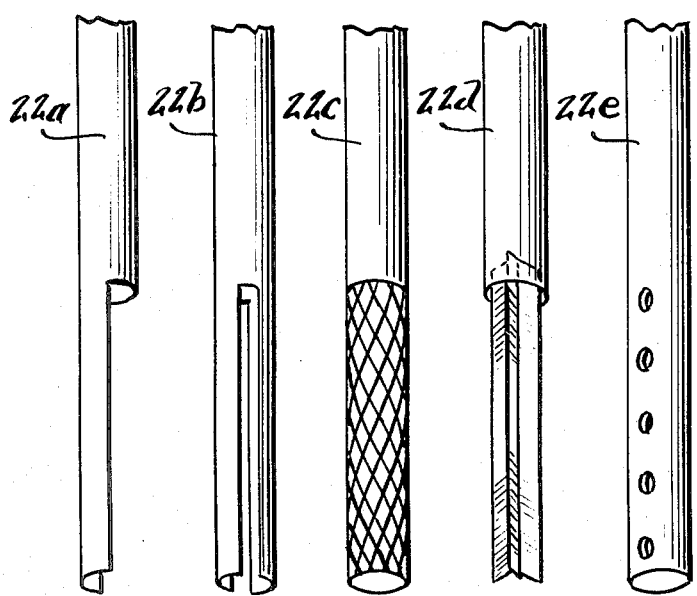
FIG. 6 illustrates several examples of the slit element to be used in body cavity fluid holding containers such as shown in FIG. 5.

It is preferred for reasons of convenience in use and safety that the body cavity fluid holding container 1 and the treated body cavity fluid holding container 5 are disposable containers, such as transfusion fluid bags and blood bags made of plasticized polyvinyl chloride. In addition to such commercially available bags for medical use, a container having a means for removing the body cavity fluid from the surface portion of the fluid, such as shown in FIG. 5, is especially preferred, since simultaneous removal of that portion of fibrin which has precipitated to the container bottom is reduced, whereby blockage of the concentrator or filter membranes can be prevented. The main body 20 of the container shown in FIG. 5 is made of a flexible material, such as a polyvinyl chloride, polyethylene or polypropylene film or sheet, and body cavity fluid outlet 21 and inlet 23 are disposed in the upper part of said main body. Within the main body, there is disposed a slit element 22 connected to said outlet 21. The slit element may be of any form and shape, such as shown in FIG. 6, so long as the body cavity fluid can easily flow into the outlet 21 even when the slit element is in close contact with the main body inside surface. When the body cavity fluid is taken out of the container, that part of the main body of the container which is situated above the fluid level surface collapses under the negative pressure in the container and thereby comes into close contact with the slit element, whereby a passage-way for the body cavity fluid is formed and the fluid is always taken out from the fluid surface portion. Therefore, the fibrin precipitate remains on the bottom and scarcely flows out into the flow path.

The concentrator to be used in the apparatus of the present invention comprises a membrane capable of prohibiting permeation of useful proteins contained in the body cavity fluid but allowing permeation of excess water contained in the body cavity fluid. Suitable examples of the membrane material which can meet these requirements are those materials known to be useful in artificial kidneys, including membranes made of cuproammonium rayon, ethylene-vinyl alcohol copolymers, polyacrylonitrile, polymethyl methacrylate, polysulfones, cellulose or cellulose derivatives. The membrane can have the form of hollow fibers, film, coil or tube, for instance. Preferred are hollow fiber membranes. In particular, hollow fibers made of ethylene-vinyl alcohol copolymers are best suited for use in the concentrator of the present invention because of their treating capacity and processability.

The filter to be used in accordance with the invention comprises a membrane capable of allowing permeation of useful substances contained in the body cavity fluid that has been concentrated in the above-mentioned concentrator, such as proteins (e.g. albumin and globulin), but prohibiting permeation of harmful substances such as bacteria or cancer cells. Examples of such membranes are membrane filters having pore sizes of 0.01 to 1 microns and made of cellulose acetate, cellulose esters and the like as well as membranes made of polyvinyl alcohol, polysulfones, polymethyl methacrylates, polypropylene (macroporous membranes), and the like, preferably in the form of hollow fibers. Hollow fibers made of polyvinyl alcohol are especially preferred.

Any pump can be used in accordance with the present invention so long as it can circulate the body cavity fluid and is non-toxic and non-hazardous to the living body. Commercially available blood pumps generally have such a function and are suitable for use.

In some cases, the use of an exchangeable prefilter in the concentration of filtration flow paths may also be useful.

FIG. 2 and FIG. 3 illustrate two modes of use of the body cavity fluid concentration and filtration apparatus of the present invention.

FIG. 2 illustrates the concentration operation. As mentioned previously, body cavity fluid removed from a body cavity and stored in container 1 can be removed from the container by means of the body cavity fluid take-out pump 2. The body cavity fluid passes through a pressure detector 13, and is led to the concentrator 3. The removal of the body cavity fluid from the body cavity can be effected either prior to the treatment operation or during the concentration operation. The body cavity fluid that has been concentrated in concentrator 3 is returned to the above-mentioned container 1, forming a circulation flow path.

The flow paths 6 and 7, which connect the above-mentioned body cavity fluid holding container 1 with the inlets of the concentrator 3 and filter 4 and with the outlets thereof, each comprises, respectively, a branched tube. While the body cavity fluid is being concentrated, those branches of the branched tubes in said flow paths 6 and 7 which are connected to the inlet and outlet of the filter are closed by means of flow path closing means. While such closing means can be of any type, the use of pinch cocks, forceps, clamps or clips, which press the passage-ways from the outside and hold them in the closed state, is most convenient. Electrically operable valves can also be used, and in this case, change-over from the concentrator to the filter can be made automatically by using a timer, for instance, whereby semi-continuous treatment becomes possible.

The filtration pressure in the concentrator can be adjusted by the pressure detector 13 and a pressure adjusting means 12 disposed in the flow path 7 connecting the concentrator 3 and the container 1. While an automatic valve operable in association with a pressure meter can be used as such pressure adjusting means, manual adjustment with a commercially available clamp or clip with simultaneous observation of a pressure meter 15 by the eye is generally most convenient. Generally, it is preferred to maintain said pressure at 500 mmHg or below.

The filtrate coming out of the concentrator discharges into a container 14 through a line 9 connected to the outlet of the concentrator. Measurement of the amount of filtrate by using a measuring cylinder as the container 14, for instance, enables comparison between the volume of body cavity fluid before concentration and the filtrate volume in the course of concentration, and thus makes it possible to easily control the degree of concentration of the body cavity fluid to a predetermined value.

Naturally, it is also possible to employ a vacuum pump in the flow path on the outlet side of the concentrator or use a suction line generally installed at the hospital bedside and thereby perform the concentration procedure under subatmospheric pressure.

When the predetermined degree of concentration is attained by recycling the body cavity fluid through the above-mentioned flow path for concentration, those branches of the branched tubes which are connected to the body cavity fluid inlet and outlet of the concentrator 3 are closed by means of pinch cocks 11, for instance, whereas the closing means 10 disposed on the branches connected to the body cavity fluid inlet and outlet of the filter 4 are removed. Thereafter, the concentrated body cavity fluid stored in the container 1 is removed by means of the pump 2, for commencement of the filtration process (cf. FIG. 3). The filtered body cavity fluid concentrate passes through a flow path 8 connected to the filtrate outlet to the container 5 and is stored therein. The filtration pressure in the filter can be detected by the pressure detector 13 used during the concentration step.

The pressure detector used in the apparatus of the present invention can conveniently be a pressure detector of the type generally used for pressure detection in blood circuits and comprises a pressure meter connected to a drip chamber. Other types of pressure detectors may also be used.

The body cavity fluid treating apparatus of the present invention may also be fitted, at any point until the body cavity fluid enters the concentrator 3, with a calcium concentration adjustment means using an ion exchange resin or a means for adding heparin, urokinase or sodium citrate for prevention of fibrin formation, as disclosed, for example in Japanese Patent Application laid open under Nos. 80-76654, 80-86456, 80-91360 and 80-91361.

FIG. 4 is a front elevation view of one example of the apparatus of the present invention. The apparatus comprises a monitoring section 16 with a roller pump 2 for transporting the body cavity fluid, a pressure meter 15, operating switches and an alarm signal device built in, and a graphic panel section 19 illustrating the manner in which the flow paths are converted and the disposition of the filter and concentrator.

At both ends of the upper side of the graphic panel 19, there are provided hooks 18 and 18' for suspending a body cavity fluid holding bag 1 and a filtered body cavity fluid concentrate holding bag 5. In front of the graphic panel 19, a pressure detector 13, a concentrator 3 and a filter 4 are respectively mounted with holders.

Flow path 6 commences at the lower end of the body cavity fluid holding bag 1 suspended on the hook 18 and connects with the body cavity fluid inlet, respectively, of the concentrator 3 and the filter 4 by means of a branched tube. In said flow path 6, there is provided the pressure detector 13 for detecting the pressure within the flow path. If an abnormal pressure is detected, the alarm signal device activates and issues a warning signal and simultaneously stops the body cavity fluid transporting pump, whereby breakage of the concentrator, filter and flow path tubes can be prevented. The body cavity fluid outlets of the concentrator 3 and filter 4 are connected with the above-mentioned bag 1 by means of the flow path 7 also comprising a branched tube. Flow path 9 connects the filtrate outlet of concentrator 3 with a measuring cylinder 14. On the other hand, the filtrate coming from the filter 4, namely the filtered body cavity fluid concentrate, is conducted by flow path 8, from the filtrate outlet of said filter to bag 5 for holding the filtered body cavity fluid concentrate. The previously mentioned flow path 7 is provided with a forceps or similar clamp means for adjusting the concentration pressure. Said apparatus is very compact, for example 600 mm in height, 40 mm in width, 300 mm in depth and 20 kg in weight, and can easily be carried owing to a handle 17 mounted on the top of the apparatus.

By using the above-mentioned apparatus of the present invention for batch-wise concentration and filtration of body cavity fluids, the processes of removing bacteria and unnecessary cellular components and concentrating useful proteins for intravenous return to the patient can be carried out in a very safe and simple manner. Moreover, this system has other advantages. Thus, for example, the final filtrate volume can easily be controlled in accordance with a preliminarily calculated value, and a high degree of safety can be secured since bacteria, cancer cells and other unnecessary materials are filtered off prior to return of the concentrate to the living body by intravenous infusion.

The present invention is further illustrated in more detail by the following example, which is by no means limitative of the present invention.

EXAMPLE

The apparatus shown in FIG. 4 was used for treating ascitic fluid. The concentrator used comprised 4,000 built-in ethylene vinyl alcohol copolymer hollow fiber pieces (350 microns in outside diameter, 250 microns in inside diameter, and 220 mm in effective length) capable of allowing permeation of substances having molecular weights less than 40,000. The filter used comprised 1,000 built-in polyvinyl alcohol hollow fiber pieces (800 microns in outside diameter, 400 microns in inside diameter, 150 mm in effective length, and 0.20 microns in average pore size).

Into a commercial bag for transfusion fluids, there was introduced 3,600 ml of ascitic fluid (with a total protein level of 2.2 g/dl). The ascitic fluid was concentrated by circulating the same at a rate of 100 cc/min. After about 80 minutes, 2,100 ml of a filtrate and 1,500 ml of an about 2.3 times concentrated ascitic fluid were obtained. Then, the flow path was switched over to the filter by means of forceps, and the filtration process was carried out at an average filtration pressure of about 150 mmHg for about 30 minutes. Throughout the above ascitic fluid treatment, no trouble was encountered and the concentration and filtration proceeded smoothly.

What is claimed is:

1. A body cavity fluid treating apparatus which comprises a first container (1) for holding a body cavity fluid, a second container (5) for holding a concentrated body cavity fluid freed from bacteria, a pump (2) for drawing out the body cavity fluid from said first container, a concentrator (3) for concentrating the body cavity fluid, a filter (4) for filtering the body cavity fluid which has been concentrated in said concentrator, a first flow path (6) connecting said first container with the body cavity fluid inlet of the concentrator and with the body cavity fluid inlet of the filter by means of a branched tube, a second flow path (7) connecting body cavity outlet of the concentrator and the body cavity fluid outlet of the filter, respectively, with said first container by means of a branched tube, a third flow path (8) connecting the filtrate outlet of the filter with said second container, a fourth flow path (9) connected to the filtrate outlet of the concentrator, means for closing, during the period of body cavity fluid concentration, those branches of the branched tubes in the first and second flow path which are connected to the inlet and outlet of the filter, respectively, and closing, during the period of body cavity fluid filtration, those branches of the branched tubes in said same flow path which are connected to the inlet and outlet of the concentrator, respectively, and a pressure adjusting means provided in the second circuit.

2. A body cavity fluid treating apparatus as claimed in claim 1, wherein said body cavity fluid is ascitic fluid.

3. A body cavity fluid treating apparatus as claimed in claim 1 or 2, wherein said container for holding a body cavity fluid is provided with a means for removing the body cavity fluid successively from the surface portion of said fluid.

4. A body cavity fluid treating apparatus as claimed in claim 3, wherein said means for removing the body cavity fluid successively from the surface portion of said fluid comprises a body cavity fluid outlet which is disposed in the upper part of the body cavity fluid holding container, and a slit element connected to said outlet and disposed within said container.

* * * * *